United States Patent [19]
Roberts et al.

[11] Patent Number: 5,596,095
[45] Date of Patent: Jan. 21, 1997

[54] FORMATION AND UTILITY OF SULFONIC ACID PROTECTING GROUPS

[75] Inventors: John C. Roberts, Newton; Raymond J. Patch, Framingham, both of Mass.

[73] Assignee: Procept, Inc., Cambridge, Mass.

[21] Appl. No.: 440,547

[22] Filed: May 12, 1995

Related U.S. Application Data

[62] Division of Ser. No. 353,832, Dec. 12, 1994.

[51] Int. Cl.$^6$ ........................ C07D 501/60; A61K 31/545
[52] U.S. Cl. ........................ 540/226; 540/224; 540/225; 540/342; 544/238; 546/324; 548/369.1; 549/72; 549/408; 552/540; 552/544; 558/46; 558/47; 558/49; 558/50
[58] Field of Search .................................. 540/226, 224, 540/225, 342; 514/204, 169, 182, 197, 203, 252, 354, 404, 448, 456, 517; 544/238; 546/324; 548/369.1; 549/72,408; 552/540, 544; 558/46, 47, 49, 50

[56] References Cited

U.S. PATENT DOCUMENTS

| | | | |
|---|---|---|---|
| 4,048,311 | 9/1977 | Berges | 424/246 |
| 4,692,441 | 9/1987 | Alexander et al. | 514/194 |

OTHER PUBLICATIONS

Truce, W. E. and Veencur, D. J., "α Alkylationn of Alkyl Alkanesulfonates," *The Journal of Organic Chemistry*, 35(4):1226–1227 (Apr. 1970).

King, S. W. et al., "Interaction of Carboxypeptidase A with Carbamate and Carbonate Esters," *Biochemistry*, 26:2294–2300 (1987).

Tunek, A. et al., "Hydrolysis of $^3$H–Bambuterol, A Carbamate Prodrug of Terbutaline, In Blood from Humans and Laboratory Animals, In Vitro," *Biochemical Pharmacology*, 37(20):3867–3876 (1988).

Saari, W. A. et al., "Cyclization–Activated Prodrugs. Basic Carbamates of 4–Hydroxyanisole," *J. Med. Chem.*, 33:97–101 (1990).

Musicki, B. and Widlanski, T. S., "Synthesis of Carbohydrate Sulfonates and Sulfonate Esters," *The Journal of Organic Chemmistry*, 55(14):4231–4233 (Jul. 6, 1990).

Musicki, B. and Widlanski, T. S., "Synthesis of Nucleoside Sulfonates and Sulfones," *Tetrahedron Letters*, 32(10:1267–1270 (1991).

Huang, J. et al., "Synthesis of Sulfonate–Linked DNA," *J. Org. Chem.*, 59:3520–3521 (1994).

*Primary Examiner*—Gary Geist
*Assistant Examiner*—Barbara S. Frazier
*Attorney, Agent, or Firm*—Hamilton, Brook, Smith & Reynolds, P.C.

[57] ABSTRACT

The present invention is a method of protecting a sulfonic acid functional group in an organic molecule as a substituted or unsubstituted neopentyl sulfonate ester. The method allows the conversion of R—SO$_3$—H to R'—SO$_3$—H, wherein R and R' are different organic radicals. Also disclosed is a method of increasing the bioavailability of drugs with a sulfonic acid functional group by protecting the sulfonic acid functional group as a substituted neopentyl sulfonate ester which has a masked heteroatom nucleophile. The masked nucleophile can be liberated in vivo, resulting in removal of the neopentyl protecting group and regeneration of the parent drug.

11 Claims, No Drawings

FORMATION AND UTILITY OF SULFONIC ACID PROTECTING GROUPS

RELATED APPLICATION

This application is a division of co-pending application Ser. No. 08/353,832 filed Dec. 12, 1994, which is incorporated herein by reference in its entirety.

BACKGROUND OF THE INVENTION

Chemical manipulations of molecules containing sulfonic acid functional groups are not widespread, largely due to solubility and charge constraints of such molecules. For example, the scope of chemical reactions of molecules containing sulfonic acids is quite limited and must be carried out in very polar solvents such as water, dimethyl sulfoxide or dimethylformamide. Isolation of the final product can be difficult due to the polar nature of such molecules, which causes their solubility in these solvents to often be very high. In addition, many reagents frequently used in standard organic chemical synthesis require non-polar solvents in which compounds containing sulfonic acids generally do not dissolve.

Having a suitable protecting group for the sulfonic acid moiety would be of significant value in organic synthesis in allowing for a greater range of possible synthetic transformations, the ability to operate in typical non-aqueous organic solvents and a more general use of standard organic chemistry techniques. Present groups used for the protection of sulfonic acids have significant disadvantages. For example, sulfonamides derived from secondary amines, while readily prepared and stable to a variety of reaction conditions, typically require harsh conditions for hydrolysis which often cause modification of other functional groups in the molecule. Furthermore, isolation of the sulfonic acid from such hydrolysis mixtures is often difficult. Isopropyl sulfonate esters have also been used as sulfonic acid protecting groups, but are cleaved by iodide and boiling methanolid ammonia (Musicki and Widlanski, *J. Org. Chem.*, 55:4231 (1990) and *Tetrahedron Letters*, 32:1267 (1991). Consequently, isopropyl sulfonate esters are incompatible with iodide reagents, for example in the Finkelstein reaction (March, Advanced Chemistry, 3rd edition, John Wiley and Sons, 1985), and with amine reagents, for example in forming Schiff bases. Sulfonic acids are also prevalent in molecules having various activities in vitro and in vivo including antiviral activities (such as anti-HIV, anti-HSV and anti-CMV activity). Compounds containing sulfonic acid groups with antiviral activities are disclosed in U.S. Ser. No. 08/156,443, U.S. Ser. No. 08/245,619 and "Compounds for Inhibiting HIV Infectivity" by Raymond J. Patch, John C. Roberts, Huai Gao and Peter V. Pallai (PRO94-03), filed concurrently in an application for a U.S. Patent, the teachings of which are hereby incorporated into this application by reference. Bioavailability can be improved if these ionized groups can be masked during passage through biological membranes. A method of decreasing the extent of ionization and increasing the lipophilicity of sulfonic acid functional groups is therefore needed to improve bioavailability in vivo.

SUMMARY OF THE INVENTION

The present invention is a method of protecting a sulfonic acid functional group in a molecule containing a sulfonic acid functional group bonded to an organic radical. The method comprises conversion of the sulfonic acid functional group to a substituted or unsubstituted neopentyl sulfonate ester, thereby protecting the sulfonic acid group from interfering with subsequent transformations. The molecule with the protected sulfonic acid group is contacted with one or more reagents under conditions suitable for modifying the organic radical or purifying the compound. The reaction product is contacted with one or more reagents under conditions suitable for converting the substituted or unsubstituted neopentyl sulfonate ester to a sulfonic acid group, thereby deprotecting the sulfonic acid group. A molecule is thereby produced comprising a sulfonic acid functional group bonded to a modified organic radical.

The sulfonic acid protecting group of the present invention has the advantage that it is stable to a wide variety of reagents and reaction conditions which are routinely used in the art of organic chemistry. In addition, sulfonic acids can be protected as sulfonate esters using the protecting groups of the present invention and then deprotected in high yield under mild conditions so that other functionalities in the organic molecule are not chemically altered.

Another embodiment of the present invention is a method of increasing the bioavailability in an individual or animal of a drug containing a sulfonic acid functional group. The method comprises administering to the individual or animal a therapeutically effective amount of a derivative of the drug in which the sulfonic acid functional group in the drug is protected as a substituted neopentyl sulfonate ester that contains a masked or derivatized nucleophilic heteroatom. The derivative on the nucleophilic heteroatom is removable in vivo, thereby unmasking the nucleophilic heteroatom. The unmasked nucleophilic heteroatom is suitably located in the molecule to cause an internal nucleophilic displacement of the sulfonate group, thereby regenerating the drug in the free sulfonic acid or sulfonic acid salt form.

Yet another embodiment of the present invention refers to a pro-drug comprising a substituted neopentyl sulfonate ester derivative of a drug containing a sulfonic acid functional group. The neopentyl group is removed in-vivo by the unmasking of a nucleophilic heteroatom in the substituted neopentyl moiety, thereby generating the drug in the free sulfonic acid or sulfonic acid salt form. Use of the pro-drug with a protected sulfonic acid increases the bioavailability of the drug.

DETAILED DESCRIPTION OF THE INVENTION

The present invention is based on the discovery that neopentyl sulfonate esters are stable to a wide variety of reagents commonly used in organic synthesis and yet can be readily converted to sulfonic acids by suitable nucleophilic reagents, for example sterically non-hindered nucleophiles, such as tetraalkyl ammonium chlorides, without chemically altering other functional groups in the molecule. As a result, neopentyl groups can serve as useful protecting groups in organic synthesis.

As used herein, a "protecting group" is a derivative of a functional group in a molecule which permits a synthetic operation to be performed on the molecule which would be less efficient or unfeasible if the functional group was not derivatized, i.e. if the functional group was "unprotected". For example, functional group protection is employed when one or more reagents are being used to selectively (or non-selectively) modify a functional group or groups in a molecule containing multiple functionalities that can be chemically modified by the reagents. Optionally, the chemical group being modified can be an unprotected sulfonic acid. In these examples, the protecting group is used to render functional group(s) less reactive towards one or more reagents, thereby allowing additional functional group(s) to be selectively (or, at times, non-selectively) modified. A protecting group can also be used to prevent the underivatized functional group from deactivating or "quenching" the reagent. For example, sulfonic acids are proton donors which can quench anionic carbon reagents such as alkyllithiums or Grignard reagents. A functional group is also protected in order that the derivatized molecule is soluble in a solvent in which the underivatized molecule is not soluble. Solubilizing a molecule in this manner is often done in order to react the molecule with reagents that require certain solvents to react in the desired manner. Such solubilization may also be used advantageously for purification of the sulfonic acid containing molecule by more routine or conventional methods, such as normal phase column chromatography or crystallization. Reagents which require that a functional group in a molecule be protected for any of the above-mentioned reasons in order that the reagents react as desired with the molecule are said to be "incompatible" with the unprotected functional group. A functional group in a molecule is therefore protected when a reagent is being used to modify the molecule and the reagent is incompatible with the unprotected functional group. After modification of the molecule, the protecting group is typically removed to regenerate the original functional group.

One embodiment of the present invention is a method of protecting a sulfonic acid group in an organic molecule containing a sulfonic acid group. The method comprises a first step in which a compound having the structure of Formula I, wherein R is an organic radical, $$R—SO_3H \qquad (I)$$

is contacted with one or more reagents under conditions suitable for converting the compound to a compound of Formula II:

$$R—SO_3—Y \qquad (II)$$

Y is a substituted or unsubstituted neopentyl group and R is defined above. The sulfonic acid group is thereby protected.

The compound of Formula II is contacted with one or more reagents under conditions for converting the compound to a compound of Formula III:

$$R'SO_3—Y \qquad (III)$$

R' is an organic radical different from R and Y is defined above.

In another aspect the compound of Structural Formula (I) is converted to a compound of Structural Formula (II) in order to carry out a transformation, such as reaction or purification by e.g., crystallization or normal phase chromatography, that can be difficult with an unprotected sulfonic acid. In this aspect the organic radical R may be converted, either before or after the transformation to another organic radical R' prior to deprotection. Alternatively, the sulfonic can be deprotected after the transformation without converting of the organic radical R to organic radical R'.

The compound of Formula III is contacted with one or more reagents under conditions suitable for removing the neopentyl group, thereby forming a compound of Formula IV.

$$R'—SO_3H \qquad (IV)$$

The sulfonic acid group is thereby deprotected.

As used herein, "neopentyl" refers to a group containing a methylene carbon atom which is bonded to a carbon containing three additional non-hydrogen substituents, two of which are carbon. Suitable non-hydrogen substituents include oxygen, nitrogen, carbon, sulfur and halogens such as chlorine, bromine and iodine. "Substituted neopentyl" refers to a neopentyl group substituted with one or more substituted or unsubstituted aryl, heteroaryl or lower alkyl groups. "Aryl" groups are defined to include substituted or unsubstituted carbocyclic aromatic rings or ring systems such as phenyl, naphthyl, tetrahydronaphthyl, biphenyl, binaphthyl, phenylalkylphenyl, phenylalkenylphenyl, phenoxyphenyl, phenylthiophenyl and phenoxyalkoxyphenyl, for example. "Heteroaryl" groups are defined to include pyridinyl, pyrimidinyl, quinolinyl, thiophenyl, furanyl, pyrazolyl, imidazolyl, benzothiophenyl, benzofuranyl, benzopyranyl, pyrrolyl and thiazolyl. "Lower alkyl" groups are defined to include aliphatic hydrocarbons having between 1 and about 8 carbons and are straight chain, branched or cyclic and can be saturated or unsaturated. Suitable substituents on the aryl, heteroaryl and lower alkyl groups include groups relatively inert to the sulfonate ester, such as lower alkyl, aryl, heteroaryl, alkoxyl, halo, —NO$_2$, —CF$_3$, —CN, and thioalkyl. Alternatively, the substituents can be, themselves, a protected nucleophilic group such as a trisubstituted silyloxy (wherein the substituents are, for example, aryl, lower alkyl or a combination thereof), carbamate, carbonate, amide, thiocarbamate, alkanoyloxy, aryloyloxy, alkanoylthiol, aryloylthiol, which, when deprotected can be reactive with the sulfonic ester. Preferably, substituents on the neopentyl group are compatible with the one or more reagents being used to modify the organic radical. As used herein, "organic radical" includes a substituted or unsubstituted aliphatic, aromatic or heterocyclic moiety to which a sulfonic acid group can be bonded.

In a preferred embodiment the neopentyl group Y has the structure shown in Formula V:

$$\begin{array}{c} R^1 \\ | \\ —CH_2—C—R^2 \\ | \\ R^3 \end{array} \qquad (V)$$

R$^1$, R$^2$ and R$^3$ are independently selected from the group consisting of substituted or unsubstituted lower alkyl, aryl substituted alkyl, heteroaryl substituted alkyl and taken together can be cycloalkyl. In a more preferred embodiment, R$^1$, R$^2$ and R$^3$ are each methyl.

In another preferred embodiment R$^3$ is a masked nucleophile or substituted lower alkyl group containing a masked or protected nucleophile. As used herein, a "masked nucleophile" is a functional group containing a nucleophilic moiety which has been derivatized with a functionality that is readily and selectively removed, preferably under mild conditions. Alternatively, "a masked nucleophile" is a functional group that is selectively convertible into a nucleophilic moiety, for example, by a chemical reaction such as reduction or oxidation. "Removing a masking" group refers to deprotecting the nucleophilic moiety or converting the functional group to a nucleophilic moiety by a chemical reaction. The masked group is sufficiently non-nucleophilic so that it does not displace sulfonate groups.

The masked nucleophilic heteroatom is preferably suitably situated so that when it is unmasked, it is capable of acting as an internal nucleophile which causes a nucleophilic displacement of sulfonate at the ester carbon of the neopentyl group to which the sulfonate is bonded, thereby deprotecting the sulfonic acid. The nucleophilic heteroatom is generally suitably situated to cause an internal nucleophilic displacement of sulfonate when the heteroatom is about one to six atoms, preferably one to four atoms, removed from the carbon to which the sulfonate is bonded. In addition to the deprotection of the sulfonic acid protected functional group, an about three to eight membered ring containing the nucleophilic heteroatom is formed as a by-product as indicated in Scheme I.

Suitable nucleophilic heteroatoms or groups include an alcoholic or alkoxide oxygen, a thiol or thiolate sulfur and an amino or amido nitrogen. Suitably substituted neopentyl groups which contain masked nucleophilic heteroatoms include compounds of Formula V in which $R^3$ is a lower alkyl substituted by trialkylsilyloxy, triarylsilyloxy, aryldialkylsilyloxy, alkyldiarylsilyloxy, $-SR^6$, $-SCONHR^5$, $-OCOOR^5$, $-OCOR^5$, $-OR^6$, $-NR^7CHO$, $-NR^7COR^5$, $-NR^7COOR^5$, or $-NR^7R^8$, for example. $R^5$ is independently selected from the group consisting of substituted or unsubstituted aryl, heteroaryl, lower alkyl, aryl substituted alkyl, and heteroaryl substituted alkyl. $R^6$ is a readily removable alcohol or thiol protecting group. Examples of suitable alcohol protecting groups include t-butyl, methoxymethyl, benzyl, 2-tetrahydropyranyl, 2-tetrahydrofuranyl, silyl esters (e.g. triisopropylsilyl and t-butyldimethyl silyl), trifluoracetate, 9-fluorenylmethyl, 2-methoxyethoxymethyl and various siloxymethyl groups such as t-butyldimethylsiloxymethyl, thexyldimethylsiloxymethyl and t-butyldiphenylsiloxymethyl. $R^7$ is hydrogen or a lower alkyl group. $R^8$ is a readily removable amine protecting group. Suitable amine protecting groups include carbobenzyloxy (CBZ) and tert-butoxycarbonyl (BOC). Other suitable thiol, alcohol and amine protecting groups are given in Greene, "Protecting Groups in Organic Synthesis," John Wiley and Sons, Second Edition (1991). Alternatively, the masked nucleophile can be $-NO_2$, $-CN$ or a carboxylic ester which can give a nucleophilic amine or alcohol upon reduction with a suitable reducing agent. The masked nucleophile can also be a vinyl group, which can give a nucleophilic alcohol after hydroboration, for example. $R^3$ can also be $-OR^6$, $-NR^7R^8$, $-NO_2$, $-CN$ or $-CH=CH_2$.

A specific example of a suitably substituted neopentyl protecting group with a masked nucleophilic heteroatom is the N-(tert-butoxycarbonyl) 2,2-dimethyl-4-aminobutyl group (hereinafter referred to as "NeonB"). The N-tert-butoxycarbonyl group (BOC) is a commonly used protecting group for amines in the art of organic synthesis and is known to be cleaved under a variety of acidic conditions (see Greene, "Protecting Groups in Organic Synthesis," John Wiley & Sons, Second Edition (1991)), including trifluoroacetic acid (TFA) (5% TFA in methanol

SCHEME I

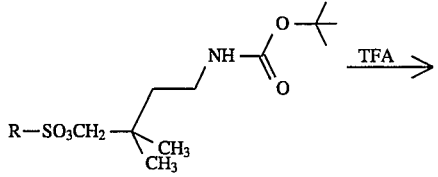

-continued
SCHEME I

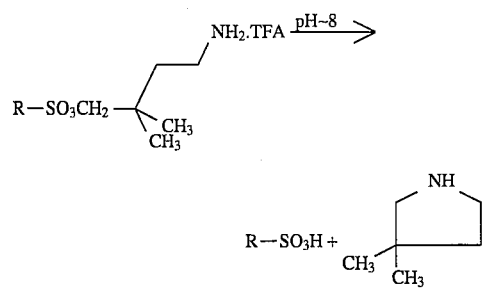

for 30 minutes) (see Example 3). After treatment of NeonB with TFA, the BOC group is liberated to give the TFA salt of the amine. Neutralization of this salt under basic conditions liberates the free amine which cyclizes intramolecularly to afford the sulfonic acid and dimethylpyrrolidine. The TFA salt is neutralized, for example, at pH greater than about 7.0, and preferably at a pH of about 8.0.

BOC groups are stable under the mildly basic conditions, such as those used in solid phase coupling techniques, for example alkylation and acylation reactions. (M. Bodanszky, "Principles of Peptide Synthesis," Second Edition, Springer Laboratory (1993)). Therefore, NeonB is suitable for use as a protecting group in solid phase reactions.

Other specific examples of a substituted neopentyl with a masked nucleophilic heteroatom suitable for use as a sulfonic acid protecting group are derived from a monoprotected 2,2-dimethylpropane-1,3-diol such as mono-O-(acyl)-, mono-O-(triarylsilyl)- or mono-O-(trialkylsilyl)-derivatives. Other examples can be synthesized by protecting the alcohol functional group of a 3-hydroxy-(2,2-dimethyl)propyl sulfonate ester, which is prepared by reacting an excess of 2,2-dimethylpropane-1,3-diol with the sulfonic acid (see Example 4). Examples of other suitable alcohol protecting groups are provided in Greene, "Protecting Groups in Organic Synthesis," John Wiley & Sons, Second Edition (1991), and are within the scope of the present invention. A nucleophilic oxygen anion can be liberated from the silyl protected alcohols, for example, by treatment with one or more equivalents of fluoride anion, according to methods known to those skilled in the art. A nucleophilic oxygen anion can also be liberated from the acyl protected alcohol by treatment with a suitable base such as hydroxide or methoxide, also according to methods known to those skilled in the art.

In another preferred embodiment $R^3$ contains one or two electron withdrawing groups bonded to a methylene or methine carbon, respectively, such that the carbon can be deprotonated to form a carbon anion. The anion is suitably situated to cause an internal nucleophilic displacement at the methylene carbon to which the sulfonate is bound, thereby deprotecting the sulfonic acid and also forming a carbocyclic ring. The anion is formed on a carbon that is one to six atoms removed from the methylene to which the sulfonate is bonded, preferably one to four atoms. Suitable electron withdrawing groups include $-NO_2$, $-CN$, malonyl, cyclic malonyl, sulfone, or combinations thereof.

Sulfonic acids are converted to neopentyl sulfonate esters by methods known to those skilled in the art of organic chemistry in which a sulfonic acid is converted to a sulfonate ester. Typically, the sulfonic acid converted into a new functional group in which the "—OH" moiety on the sulfonic acid is replaced with a good leaving group such as chloride, bromide or iodide. Chloride is preferred. Sulfonyl chlorides can be prepared by reaction of sulfonic acids with thionyl chloride, phosphorus trichloride or phosphorus pentachloride, for example (March, "Advanced Organic Chemistry" Third Edition, John Wiley & Sons (1985) (see Scheme 2). The resulting sulfonyl chloride is then reacted with a suitable neopentyl alcohol, such as neopentyl alcohol or mono-protected 2,2-dimethylpropane-1,3-diol, or an excess of 2,2-dimethylpropane-1,3-diol in the presence of a base, such as pyridine or triethylamine, to give the neopentyl sulfonate ester (see Examples 2 and 4). It is possible to protect more than one sulfonic acid functional group in a molecule at one time. The reaction sequence from sulfonic acid to neopentyl sulfonate ester is exemplified in Scheme II).

SCHEME II

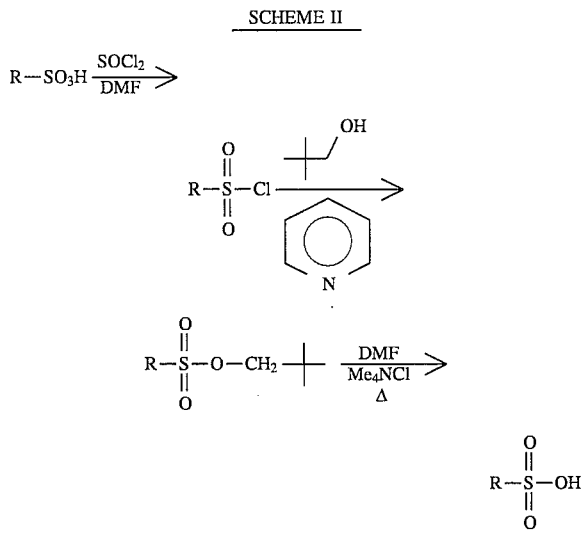

The one or more reagents which are contacted with a compound having the structure of Formula II react preferentially with the organic radical portion of the molecule over the sulfonate ester. Preferably, the sulfonate ester is inert towards and compatible with the reagents. It is to be understood that more than one functional group in the organic radical, and indeed more than one kind of functional group can be simultaneously modified in one reaction while the sulfonic acid functional group is protected (e.g. aldehydes, ketones and acids can be simultaneously reduced with a borane reducing agent). More than one reagent can be used as required to convert R—$SO_3$—Y to R'—$SO_3$—Y in one or more reaction steps. Alternatively, some or all of the additional reaction steps can be carried out with reagents that are non-reactive and compatible with sulfonic acid functional groups.

There are many reagents that are reactive with or incompatible with sulfonic acid functional groups but are essentially non-reactive with and/or compatible with neopentyl sulfonate esters. Examples of such reagents and reaction conditions are identified in Table 1.

TABLE 1

| Reagent | Solvent | Conditions | Time |
| --- | --- | --- | --- |
| t-BuLi | Ether/THF | −78° C. | 0.5 h |
| n-BuLi | Ether/THF | −78° C. | 1 h |
| HCl | MeOH | RT | |
| NaOH | MeOH | RT | |
| TFA/$Et_3$SiH | Neat | RT | 16 h |
| ArLi | THF | RT | 0.5 h |
| $BF_3$.$Et_2$O | $CH_2Cl_2$ | Reflux | 16 h |

TABLE 1-continued

| Reagent | Solvent | Conditions | Time |
| --- | --- | --- | --- |
| $BF_3$.$Et_2$O/TMSCN | $CH_2Cl_2$ | RT | 16 h |
| $Et_2$AlCl | $CH_2Cl_2$ | RT | 16 h |
| $B_2H_6$ | THF | Reflux | 5 h |
| NaI | Acetone | Reflux | 16 h |
| NaI | DMF | 105° C. | 12 h |
| MsCl/TEA | $CH_2Cl_2$ | RT | 2 h |
| Piperidine | DMF | 70° C. | 1 h |
| $NaBH_2$ | TFA | 00 to RT | 0.5 h |
| $H_2$, Pd—C | EtOAc | 1000 psi; RT | 16 h |
| $H_2$, $PtO_2$ | EtOAc | 1400 psi; 120° C. | 16 h |
| $NaCNBH_3$ | MeOH; 1° amine | RT | 16 h |
| DIBAL | Toluene | RT | 1 h |
| $KMnO_4$ | t-BuOH/$H_2$O | RT | 4 h |
| $RuCl_3$/$NaIO_4$ | $CCl_4$/$CH_3$CN/$H_2$O | RT | 16 h |
| $SOCl_2$ | $CH_2Cl_2$/DMF/Tol. | Reflux | 16 h |
| $H_2$NOH | EtOH/Pyridine | 60° C. | 48 h |
| Phosphorous ylides | Chlorobenzene | Reflux | >72 h |
| TsOH | Toluene | Reflux | 24 h |
| $(COCl)_2$ | DMF | RT | 2 h |
| 10 Amines/(acid) | Toluene | Reflux | 16 h |
| KH | THF | RT | 16 h |
| NaH | THF | Reflux | 4 h |
| $CrO_3$ | $CH_2Cl_2$/Ether | RT | 8 h |
| Vinyl-MgBr | THF | Reflux | 3 h |
| $NaN_3$ | DMSO | 70° C. | 16 h |
| $Br_2$ | MeOH | RT | 16 h |
| $Ph_3P$—$Br_2$ | Dichloroethane | RT | 16 h |
| NaOMe | MeOH | RT | 48 h |
| $PBr_3$/Pyridine | Ether | RT | 2 h |
| 48% HBr | Dioxane | RT | 16 h |
| NBS/$(PhCO)_2O$ | $CCl_4$ | Reflux | 6 h |

RT = Room Temperature
TFA = Trifluoroacetic Acid
TMSCN = Trimethysilyl Cyanide
MsCl = Methanesulfonyl Chloride
THF = Tetrahydrofuran
DMF = Dimethylformamide
EtOAc = Ethyl Acetate
MeOH = Methanol
TsOH = Toluenesulfonic Acid
Tol. = Toluene
Et = Ethyl
Bu = Butyl
EtOH = Ethanol
DIBAL = Diisobutylaluminum Hydride
t-BuOH = t-Butanol
DMSO = Dimethylsulfoxide
NBS = N-Bromosuccinimide Table 1 does not provide a complete list of all reagents and/or conditions compatible with neopentyl sulfonate esters. Furthermore, the conditions listed in Table 1 are merely examples with the given reagent. Higher or lower temperatures or pressures, longer or shorter reaction times and/or different solvents can also be successfully employed in many settings.

Deprotection of neopentyl sulfonate esters can be accomplished with a suitable nucleophilic reagent (such as a sterically non-hindered nucleophile), e.g. a reagent that is sufficiently nucleophilic to cleave sulfonate esters and has sufficiently little steric bulk to allow nucleophilic attack at the carbon to which the sulfonate is bonded. Suitable nucleophilic reagents include those reagents which generate chloride anion, for example tetraalkyl ammonium chlorides, such as tetramethylammonium chloride, tetrabutylammonium chloride, dimethyldiethyl ammonium chloride, ethyltrimethyl ammonium chloride and methylethyldipropyl ammonium chloride. Suitable deprotection conditions include contacting the neopentyl sulfonate ester with about 1.0 equivalent up to about 20 equivalents of the tetraalkyl ammonium chloride, preferably about 6–12 equivalents in a solvent that promotes nucleophilic substitutions. Suitable solvents include aqueous and anhydrous dipolar aprotic solvents such as dimethyl formamide (DMF), dimethyl sulfoxide (DMSO) and hexamethylphosphoramide (HMPA). Mixtures of these solvents can also be used. In one specific example, DMF is used (see Example 7). The deprotection is generally run at an elevated temperature sufficient to cause a nucleophilic displacement of the sulfonate group at the neopentyl carbon bonded to the sulfonate without causing degradation of functional groups in other parts of the molecule. Suitable elevated temperatures can be in the range from about 120° C. to about 200° C., and is preferably from about 150° C. to about 170° C.

Another embodiment of the present invention is a compound having the structure of Formula (II). Y is a substituted or unsubstituted neopentyl group, as described above in the method of protecting a sulfonic group, and R is a substituted or unsubstituted aryl radical or heteroaryl radical.

Suitable "aryl radicals" include substituted or unsubstituted carbocyclic aromatic rings or ring systems such as phenyl, naphthyl, tetrahydronaphthyl, biphenyl, binaphthyl, phenylalkylphenyl, phenylalkenylphenyl, phenoxyphenyl, phenylthiophenyl and phenoxyalkoxyphenyl, for example. Suitable "heteroaryl radicals" include pyridinyl, pyrimidinyl, quinolinyl, thiophenyl, furanyl, pyrazolyl, imidazolyl, benzothiophenyl, benzofuranyl, benzopyranyl, pyrrolyl and thiazolyl, for example. Suitable substituents on aryl and heteroaryl radical include substituted or unsubstituted lower alkyl, alkoxyl, carbamate, halo, $-NO_2$, $-CN$, $-CF_3$, carbonate, amide, thiocarbamate, alkanoyloxy, aryloyloxy, alkanoylthiol, aryloylthiol, thioalkyl, trisubstituted siloxy, heteroaryl and aryl, for example.

In a specific example, the aromatic radical is substituted with an optionally protected aminomethyl group (i.e., $NH_2-CH_2-Ar-SO_2-O-$(neopentyl)), wherein Ar is an aromatic radical, as defined above). Phenyl and naphthyl groups are preferred aromatic radicals. These compounds can be prepared, for example from the corresponding aminoarylsulfonate by standard Sandmeyer chemistry (Vogel's Textbook of Practical Organic Chemistry, 5th edition, Longman, Scientific and Technical, (1989) page 1081) to the nitrile followed by reduction to the aminomethylarylsulfonate.

It is known that water insoluble polymers with free sulfonic acid groups can be used for ion exchange in aqueous systems and as a proton source in solid/liquid phase organic reactions, (Seto et al., Synth. Commun. 22:2823 (1992)). Aminomethylarylsulfonic acids can be incorporated into water insoluble polymeric compositions. For example, neopentyl aminomethylarylsulfonate can be reacted with acryloyl chloride. The resulting acrylamide can be copolymerized with another monomer such as dimethyl acrylamide and a suitable crosslinking reagent such as bisacryloylethylenediamine (Atherton and Sheppard, "Solid Phase Peptide Synthesis—A Practical Approach, IRL Press (1989)), which after removal of the neopentyl protecting group, yields a water insoluble polymer with free sulfonic acid groups.

When R is a substituted or unsubstituted alkyl radical, preferably $R^3$ is a masked nucleophile or a lower alkyl group substituted by a masked nucleophile, as described above. Suitable "alkyl radicals" are generally straight chain, branched chain or cyclic alkyl radicals of about four carbons up to about thirty or forty carbons. The alkyl radical can have a wide variety of substituents including but not limited to lower alkyl, alkoxyl, halo, $-CN$, $-NO_2$, $-CF_3$, carbamate, carbonate, amide, thiocarbamate, alkanoyloxy, aryloyloxy, alkanoylthiol, aryloylthiol, thioalkyl, trisubstituted siloxy, heteroaryl and aryl, for example.

Another embodiment of the present invention is a method of increasing the bioavailability of a drug having one or more sulfonic acid functional groups.

Substituted and unsubstituted neopentyl groups with masked nucleophilic heteroatoms, as described above, can be used to create pro-drugs from drugs having sulfonic acid functional groups. When the group masking the nucleophilic heteroatom is removable in vivo, the substituted neopentyl group is suitable for protecting the sulfonic acid, thereby creating a pro-drug. As used herein, "a pro-drug" is a derivatized form of a drug that is administered to an individual and which is converted or metabolized to the active form of the drug in vivo. Although a pro-drug may not be active until it is converted to the underivatized drug, it is often desirable to administer a pro-drug to the individual rather than the active form of the drug in order to optimize certain desirable properties of the drug, e.g. bioavailability or resistance to degradation. An "individual" may be a human or animal patient.

Drugs which contain sulfonic acid groups, particularly antiangiogenic polyanionic agents and anti-viral agents that interfere with viral cell adsorption such as suramin, suramin derivatives (Braddock, P. S., et al., Br. J. Cancer, 69:890–9 (1994)) or distamycin A derivatives (Ciomei, M., et al., Biochem. Pharmacol., 47:295–302 (1994)) suffer from a lack of effectiveness in vivo due in part to poor bioavailability. Suramin requires intravenous administration due to poor oral bioavailability and severe irritation when given intramuscularly (Zaniboni, A., Med. Oncol. Tumor Pharmacother., 7:287–90 (1990)).

Many polyanionic compounds having potential anti-HIV activity have been shown to interfere at various stages of viral infectivity in addition to blocking vital adsorption on target cells. Such additional mechanisms include inhibition of reverse transcription and HIV proteinase (Brinkworth, R. I. and Fairlie, D. P., Biochem. Biophys. Res. Commun., 188:624–630 (1992)). However, the ability of such compounds to effect inhibition of these viral enzymes is precluded by their inability to penetrate cell membranes.

The anionic charged nature of such compounds makes it difficult for passage through biological membranes including the blood-brain barrier. This seriously limits the usefulness of these agents in treating infections of the central nervous system. Consequently, converting antiviral and other therapeutic agents containing one or more sulfonic acid functional groups into pro-drugs, as described above, would increase the effectiveness of the agent by increasing its bioavailability, particularly when the agent is administered orally to the patient. It would also increase the access of the agent to intracellular environments.

In this embodiment the present invention includes a method comprising administering to the patient a therapeutically effective amount of a pro-drug which comprises one or more substituted neopentyl sulfonate esters of the drug. The substituted neopentyl sulfonate ester group comprises a masked nucleophilic heteroatom that is derivatized with a group that can be removed in vivo. The nucleophilic heteroatom is also suitably situated so that when it is liberated (or unmasked) it is capable of deprotecting the sulfonate functional group by intramolecular nucleophilic attack at the methylene to which the sulfonate is bonded. Generally, the nucleophilic heteroatom is suitably situated to cause the internal nucleophilic attack when the internal nucleophilic attack will result in the formation of a three to eight membered ring, preferably a three to six membered ring.

In one aspect the protected sulfonic acid functional group of the pro-drug has the structure represented by Formula I, wherein $R^1$ and $R^2$ are independently selected from the group consisting of substituted or unsubstituted lower alkyl, aryl substituted alkyl, heteroaryl substituted alkyl and taken together can be cycloalkyl. $R^3$ is a lower alkyl substituted by a nucleophilic heteroatom, for example oxygen, nitrogen or sulfur, that is protected by a functional group that is removable in vivo. Preferably, the substituent is selected from the group consisting of trialkylsilyloxy, triarylsilyloxy, aryldialkylsilyloxy, alkyldiarylsilyloxy, —OCOR$^5$, —OCOOR$^5$, —OR$^6$, —NR$^7$CHO, —NR$^7$COR$^5$, —NR$^7$COOR$^5$ or —NR$^7$R$^8$. $R^5$ can be selected from the group consisting of substituted or unsubstituted aryl, heteroaryl, lower alkyl, aryl substituted alkyl and heteroaryl substituted alkyl. $R^6$ is an alcohol protecting group capable of being removed in vivo. Examples of suitable alcohol protecting groups include t-butyl, methoxymethyl, 2-tetrahydropyranyl, 2-tetrahydrofuranyl, silyl esters (e.g. triisopropylsilyl and t-butyldimethyl silyl), trifluoracetate, 2-methoxyethoxymethyl and siloxymethyl. Other suitable alcohol protecting groups are provided in Greene, "Protective Groups in Organic Synthesis," John Wiley and Sons, Second Edition (1991), and are within the scope of the present invention. $R^7$ is hydrogen or lower alkyl. $R^8$ is an amine protecting group capable of being removed in vivo. Examples of suitable amine protecting groups include BOC and CBZ. Other suitable amine protecting groups are given in Greene, "Protecting Groups in Organic Synthesis," John Wiley and Sons, Second Edition, (1991). Alternatively, $R^3$ is —OR$^6$ or —NR$^7$R$^8$.

As discussed above, the substituent can be for example a carbamate (e.g., —NHCOOR$^5$) or formamide (—NHCHO), in which case the nucleophilic heteroatom is an amine nitrogen. A variety of carbamate groups are known to undergo spontaneous cleavage in solution at kinetically favorable rates (Saari, et al. *J. Med. Chem.*, 33:97 (1990)) and would thus be expected to degrade in vivo. Carbamates are also degraded enzymatically, (King, et al., *Biochemistry*, 26:2294 (1987)), particularly in blood, (Tunek, et al., *Biochemical Pharmacology*, 37:3867 (1988), to afford the unprotected amine. Many carbamates are known to be stable to mild acid conditions (Greene, "Protective Groups in Organic Synthesis," John Wiley and Sons, Second Edition (1991)) and would therefore be expected survive conditions in the stomach long enough after oral administration to be absorbed into the blood stream. One substituted neopentyl protecting group suitable for use in protecting sulfonic acids for the creation of pro-drugs which comprises a carbamate is NeonB.

The group can also be a carboxylic ester (e.g., —OCOR$^5$). The unmasking of esters in vivo is known to occur enzymatically by the action esterases to yield a nucleophilic alcoholic oxygen. Examples of protecting groups which can be liberated by this mechanism include derivatives of the 3-hydroxy-2,2-dimethyl propyl group (—SO$_2$—O—CH$_2$—C(CH$_3$)$_2$—CH$_2$OCOR), e.g., O—(acetyl)—, O—(butyryl)— or O—(propionyl)—.

For purposes of the method of increasing the bioavailability of a drug having sulfonic acid functional groups, preferred neopentyl substituents, such as aryl and heteroaryl groups are chosen so as to limit the toxicity, the adverse side-effects of the drug, metabolic detoxification and excretion and do not hinder unmasking of the nucleophilic heteroatom. In addition, substituents are preferably chosen so as to limit the toxicity of the cyclic by-product of the nucleophitic deprotection by the unmasked nucleophilic heteroatom, as discussed earlier. Suitable substituents for alkyl, aryl and heteroaryl groups preferably have the same characteristics discussed above for preferred aryl and heteroaryl groups.

Another embodiment of the present invention is a pro-drug comprising a substituted neopentyl sulfonate ester of a drug having one or more sulfonic acid functional groups. The drug can be a substituted or unsubstituted aryl, heteroaryl or alkyl radical with a free sulfonic acid, as described earlier for the compounds of the present invention. Suitably substituted neopentyl groups are as described above in the method for increasing the bioavailability of a drug with sulfonic acid functional groups. Suitable potential drugs with sulfonic acid functional groups include suramin and other polyanionic dyes which have antiviral activity, inhibit reverse transcriptase and/or inhibit gp120/CD4 binding (Kozlowski, M. R. and Watson, A., *Antiviral Chem. & Chemother.*, 3(1):49–53 (1992); Brinkworth, R. I. and Fairlie, D. P., *Biochem. and Biophys. Res. Commun.*, 188(2):624–630 (1992); Oesterle, R., et al., *Antiviral Res.*, 23:107–119 (1993); Thorne, H. V. and Clarke, G. F., *J. Gen. Virol.*, 64:1365–1368 (1983); Balzarini, J., et al., *Int. J. Cancer*, 37:451–457 (1986); Weaver, J. L., et al., *Antiviral Chem. Chemother.*, 3(3):147–151 (1992); "Antiviral Compositions Containing the Azo Dye Derivatives and Methods for Using the Same," (U.S. Ser. No. 07/684,258), (U.S.) Food and Drug Administration, Rockville, Md., (Apr. 12, 1991); "Azo Dye Derivatives Exhibiting Anti-HIV Activity Pharmaceutical Compositions Containing the Same and Methods for Using the Same," (U.S. Ser. No. 07/715,652), (U.S.) Department of Health and Human Services, (Jun. 14, 1991)); "Compounds for Inhibiting HIV Infectivity" (U.S. Ser. No. 08/245,619), "Compounds for Inhibiting HIV Infectivity" (U.S. Ser. No. 08/156,443); "Compounds for Inhibiting HIV Infectivity" by Raymond J. Patch, John C. Roberts, Huai Gao and Peter V. Pallai (PRO94-03) (filed concurrently herewith), the teachings of which are hereby expressly incorporated into this application by reference). Suitable drugs include Acamprosate, for alcohol withdrawal, and Dipyrone, an antipyretic. A pro-drug would increase the lipophilicity of these agents and presumably increase bioavailability to the central nervous system and thereby increase efficacy. Cefonicid is an antibacterial that must be administered intramuscularly or intraveneously. Protection as a pro-drug can allow for oral bioavailability and increased applications. Other drugs which have free sulfonic acid groups and are therefore candidates for protection as a pro-drug include Taurosteine, Glutaurine, Solasulfone, Dibupyrone, Methaniazide, Dicresulene, Cefsulodin, Cefpimizole, Sulbenicillin, and Sulfamazone. These drugs are described in greater detail in *Comprehensive Medicinal Chemistry Drug Compendium*, Volume 6, editors, C. Hansch, P. G. Sammes and J. B. Taylor, Pergamon Press (1990).

Other specific examples of compounds having potential antiviral activity which can be converted into the pro-drugs of the present invention, thereby increasing their bioavailability, are compounds having one of the following structures:

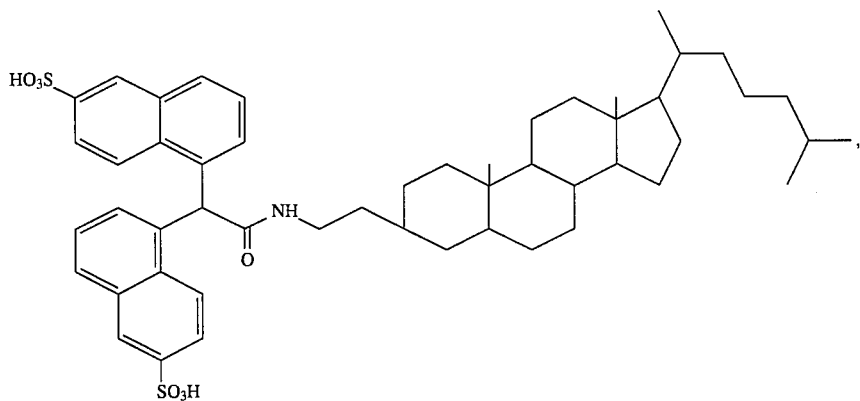
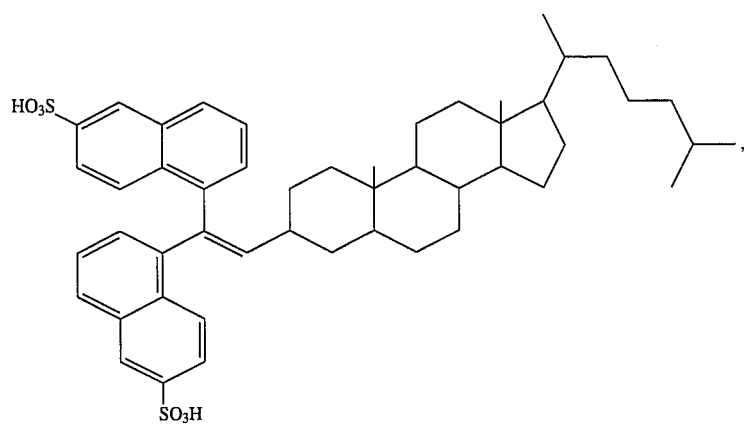
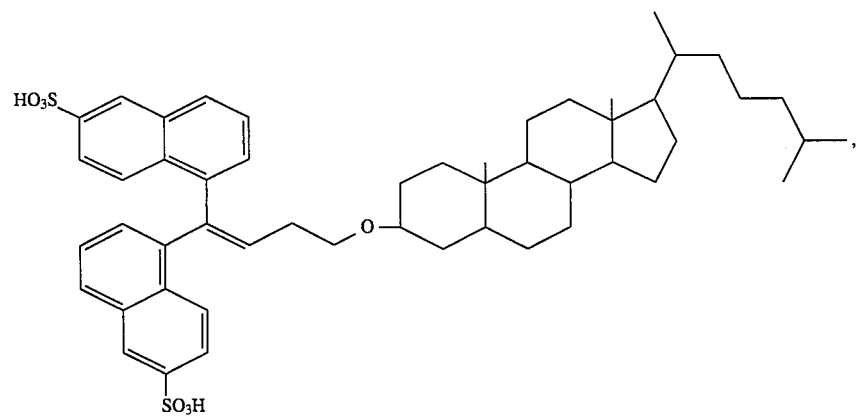
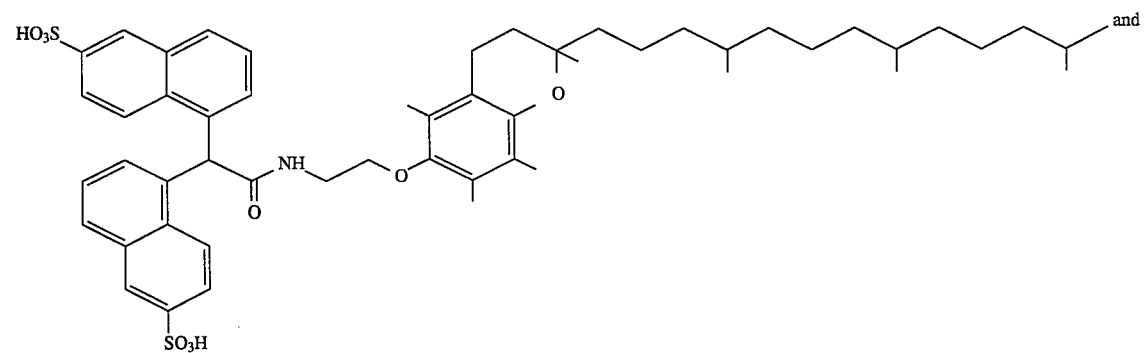

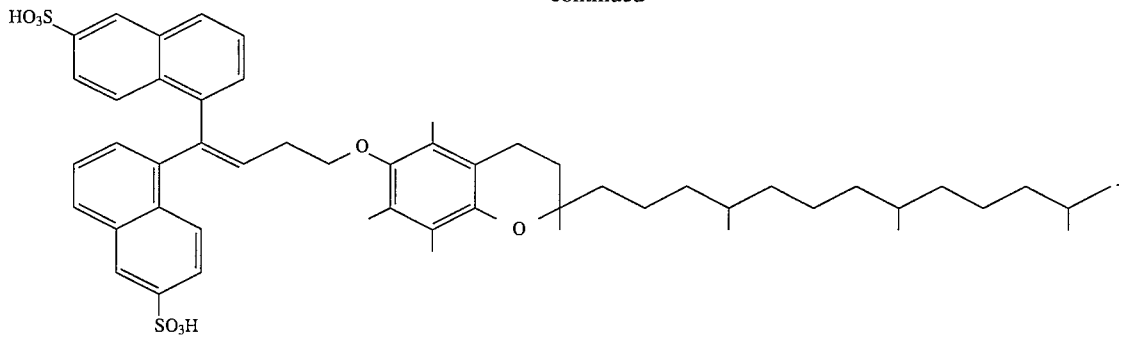

The invention is further illustrated by the following examples, which are not intended to be limiting in any way.

EXAMPLE 1

Preparation of NeonB Protecting Groups

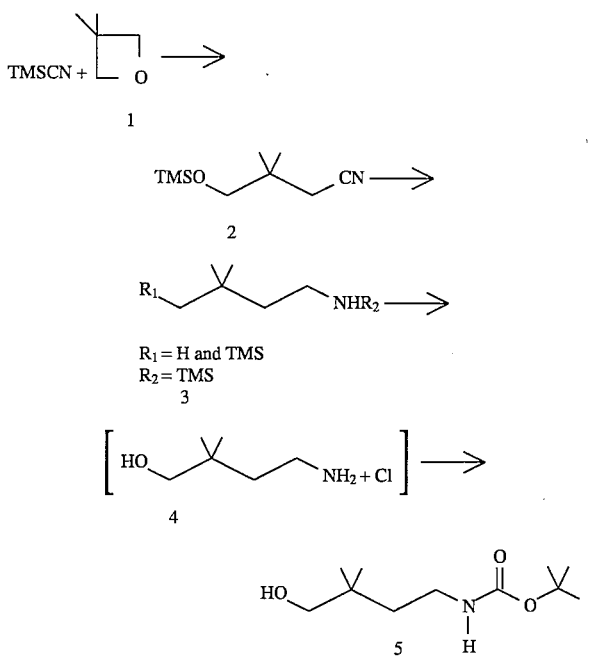

Conversion of 3,3-Dimethyloxetane (1) to Nitrile (2)

To a 500 mL flask was added 55 mL (40 grams; 41 mmol) trimethylsilyl cyanide, followed by aluminum trichloride (1.1 grams; 8.3 mmol). Over a period of 2 hours, 41 mL (34 grams; 40 mmol) of 3,3-dimethyloxetane was added dropwise. Spontaneous heating was observed. After 16 hours, the crude NMR of an aliquot indicated that nitrile 2 was produced.

Conversion of Nitrile 2 to Amine 3

Diethyl ether (250 mL) was added to nitrile 2. The solution was then cooled to 0° C. and transferred dropwise, via cannula, over 1 hour to a 2 L flask containing 1M lithium aluminum hydride in diethyl ether (1 L; 1000 mmol), stirred at 0° C. After 16 hours at room temperature, the excess reagent was quenched at 0° C. with 40 mL water, then 80 mL 5% NaOH, and then 40 mL water. The aluminum salts were filtered through a sintered glass funnel, and the ethereal solution was concentrated to a pale yellow oil (69 grams; 93% mass balance). Crude NMR indicated that product 3 consisted of a mixture of TMS-O and TMS-N compounds.

Conversion of Amine 3 to NeonB 5

Product 3 was dissolved in dioxane (200 mL). 6M aqueous hydrochloric acid (60 mL) was then added with stirring to generate amine hydrochloride 4. After 30 minutes, the reaction mixture was brought to pH 8 by the slow addition of saturated aqueous sodium bicarbonate solution and the total volume of the reaction mixture was brought to about 500 mL by the addition of water. Di-tert-butyl dicarbonate (89 grams; 410 mmol) was added portionwise and stirring was allowed to proceed for 16 hours. The mixture was concentrated to about 300 ml and extracted (3x) with ethyl acetate. The combined organics were washed with saturated aqueous ammonium chloride, water, and brine, dried over magnesium sulfate, filtered, and concentrated to afford 114 grams of a pale yellow oil. Thirteen grams of the crude product were purified by silica gel chromatography (solvent gradient of 4:1 hexane/ethyl acetate to 2:1 hexane/ethyl acetate) to obtain 6.1 grams of alcohol 5 (NeonB-OH) as a colorless oil which crystallized on standing. The remaining oil was dissolved in hot hexane (200 mL), seeded with crystals of 5 and left stoppered at 4° C. for 24 hours. The resulting colorless crystals were filtered and washed with cold hexane. After removal of residual hexane in vacuo, 37 grams of colorless crystals were obtained (total yield 50%, 4 steps). $^1$H NMR (CDCl$_3$) δ 4.67 (bs, 1H), 3.37 (s, 2H), 3.13 (m, 2H) 1.50 (m, 2H), 1.43 (s, 9H), 0.90 (s, 6H).

EXAMPLE 2

PROTECTION OF SULFONIC ACIDS WITH NeonB

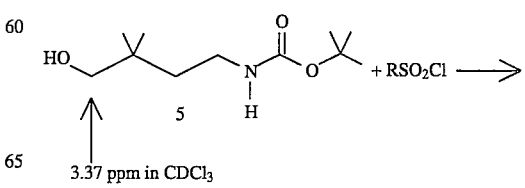

17
-continued

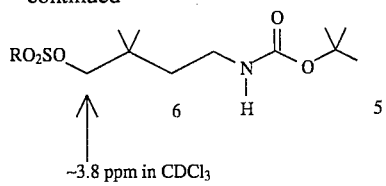

~3.8 ppm in CDCl₃

A 0.2M solution of alcohol 5 in pyridine was stirred under argon at room temperature. An equimolar amount of the sulfonyl chloride RSO₂Cl (solid, liquid, or in solution) was added in one portion. Stirring was allowed to proceed for 16 hours. The reaction mixture was diluted to five times the volume with ethyl acetate, and the resulting organic solution was washed several times with saturated aqueous copper sulfate, once with water, and once with brine, dried over magnesium sulfate, filtered, and concentrated. The products generally appeared homogenous by TLC but could be purified by silica gel chromatography if necessary. The most marked NMR change associated with the NeonB portion of the products was a downfield shift of the methylene group attached to oxygen from 3.37 ppm (in CDCl₃) in the starting material to about 3.8 ppm (in CDCl₃) in the product.

EXAMPLE 3

DEPROTECTION OF NeonB PROTECTED SULFONIC ACIDS

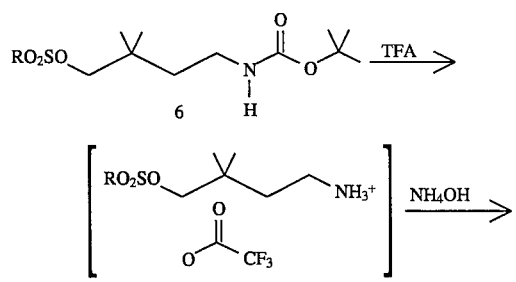

Any standard acidic conditions for removal of the tert-butyl carbamate group may be used (e.g. 0.2M in 5% TFA/methanol, 30 minutes). Concentration in vacuo followed by treatment with dilute basic solutions (e.g. 0.01M NaOH/methanol or NH₄OH/methanol, 1 minute) quantitatively provided the free sulfonic acid salt and 3,3-dimethyl pyrrolidine. The free sulfonic acid may be isolated by ion exchange chromatography.

18

EXAMPLE 4

SYNTHESIS AND DEPROTECTION OF 2,2-DIMETHYL-1,3-PROPANEDIOL PROTECTED SULFONIC ACIDS

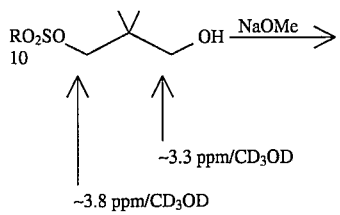

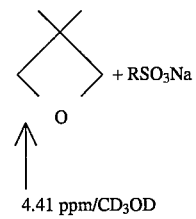

To a solution of 2,2-dimethylpropane-1,3-diol (20 mmol) in pyridine (10 mL), stirred in room temperature, was added a solution of the sulfonyl chloride (1 mmol) in pyridine (5 mL), dropwise over 1 minute. The reaction was stirred for 8–24 hours, diluted with ethyl acetate (100 mL), and washed repeatedly with 10% HCl (aqueous) until the pyridine and excess diol were removed. The organic layer was washed with water and brine, dried over magnesium sulfate, filtered, and concentrated to afford crude 10. Crude products were essentially free of impurity and mass recovery was generally greater than 85%.

A 0.05M solution of sulfonate 10 was prepared in 0.01M NaOH/methanol and heated at 50° C. until the reaction was complete as indicated by TLC or NMR (see above chemical shifts). The deprotection was generally complete in 12 hours and did not generate byproducts. Isolation of the free sulfonic acid may be accomplished by ion exchange chromatography.

EXAMPLE 5

PREPARATION OF NEOPENTYL 5-BROMONAPHTHALENE-2-SULFONATE

To a suspension of 5-bromonaphthalene-2-sulfonic acid (8 grams; 28 mmol) in 25 mL of thionyl chloride was added DMF dropwise at 5° C. (to obtain a homogeneous solution about 4 mL of DMF was added). The clear brown solution was stirred at room temperature for 2 hours. The reaction mixture was concentrated under reduced pressure and the resulting oil was poured into ice water. The off-white solid that formed was filtered and dried under reduced pressure. Yield: about 7.8 gm (92%). The material was used for the next reaction without further purification.

Solid neopentyl alcohol (2.7 grams; 30.8 mmol) was added at room temperature to a solution of 5-bromonaphthalene-2-sulfonyl chloride (8.5 grams; 28 mmol) in 40 mL of pyridine. The reaction mixture was stirred at room temperature overnight (about 16 hours). The reaction mixture was co-distilled with toluene (about 100 mL) and the resulting oil poured into water to give a pale yellow solid which was filtered and dried. The solid was further purified by silica gel chromatography (EtOAc: Hexane 1:8). Yield: 8.9 gm (89%).

EXAMPLE 6

PREPARATION OF NEOPENTYL 5-FORMYLNAPHTHALENE-2-SULFONATE

To a cooled (−80° C.) solution of neopentyl 5-bromonaphthalene-2-sulfonate (300 mg; 0.84 mmol) in anhydrous ether (12 mL) is added tert-butyllithium (1.7M in ether) (1 mL; 1.7 mmol), immediately followed by a solution of dimethylformamide (125 mg; 1.7 mmol) in ether (2 mL). The external cooling bath is removed and stirring is allowed to proceed for 1 hour. The reaction mixture is quenched with water (10 mL), the two solution phases are separated and the aqueous phase is extracted with ether (2×10 mL). The combined organic phase is dried (MgSO$_4$), filtered and concentrated under reduced pressure to afford crude neopentyl 5-methylnaphthalene-2-sulfonate.

EXAMPLE 7

DEPROTECTION OF NEOPENTYL 5-BROMONAPHTHALENE-2-SULFONATE

A mixture of neopentyl 5-bromonaphthalene-2-sulfonate (20 mg; 0.07 mmol) and tetramethylammonium chloride (70 mg; 0.64 mmol) in dimethylformamide (2 mL) is heated at 160° C. for 16 hours. The solution is then cooled to room temperature and concentrated under reduced pressure to remove most of the DMF. The residue can be purified, for example, by reversed phase preparative HPLC using a Waters 600E system equipped with a Prepack® RCM Cartridge assembly (Waters Chromatography, Division of Millipore, Milford, Mass.), C-18 column, and a gradient solvent system consisting of water, acetonitrile, methanol and 0.1% trifluoroacetic acid.

Equivalents

Those skilled in the art will know, or be able to ascertain using no more than routine experimentation, many equivalents to the specific embodiments of the invention described herein. These and all other equivalents are intended to be encompassed by the following claims.

What is claimed is:

1. A method of increasing the bioavailability in an individual or animal of a drug having one or more sulfonic acid functional groups, comprising administering to the individual a therapeutically effective amount of the corresponding pro-drug having one or more substituted-neopentyl sulfonate esters wherein the substituent is a protected nucleophilic group that is capable of being deprotected in vivo; and wherein the nucleophilic group is suitably situated so that after being deprotected it is capable of displacing the sulfonate group by internal nucleophilic attack at the ester carbon to which the sulfonate group is bonded.

2. The method of claim 1 wherein the derivatized sulfonic acid functional groups have the following structural formula:

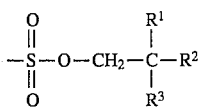

wherein $R^1$ and $R^2$ are independently selected from the group consisting of substituted or unsubstituted lower alkyl, aryl substituted alkyl, heteroaryl substituted alkyl; in the alternative, $R^1$ and $R^2$ taken together can be cycloalkyl;

wherein $R^3$ is a protected nucleophilic group capable of being deprotected in vivo or a lower alkyl substituted by a nucleophilic group that is protected with a group capable of being removed in vivo.

3. The method of claim 2 wherein $R^1$ and $R^2$ are each lower alkyl and $R^3$ is a lower alkyl substituted by trialkylsilyloxy, triarylsilyloxy, aryldialkylsilyloxy, alkyldiarylsilyloxy, —SR$^6$, —SCONHR$^5$, —OCOR$^5$, —OCOOR$^5$, —OR$^6$, —NR$^7$CHO, —NR$^7$COR$^5$, —NR$^7$COOR$^5$ or —NR$^7$R$^8$;

wherein $R^5$ is selected from the group consisting of substituted or unsubstituted aryl, heteroaryl, lower alkyl, aryl substituted alkyl and heteroaryl substituted alkyl;

wherein $R^6$ is an alcohol or thiol protecting group;

wherein $R^7$ is hydrogen or a lower alkyl group; and wherein $R^8$ is an amine protecting group.

4. The method of claim 3 wherein the drug is selected from the group of compounds having the following structural formula:

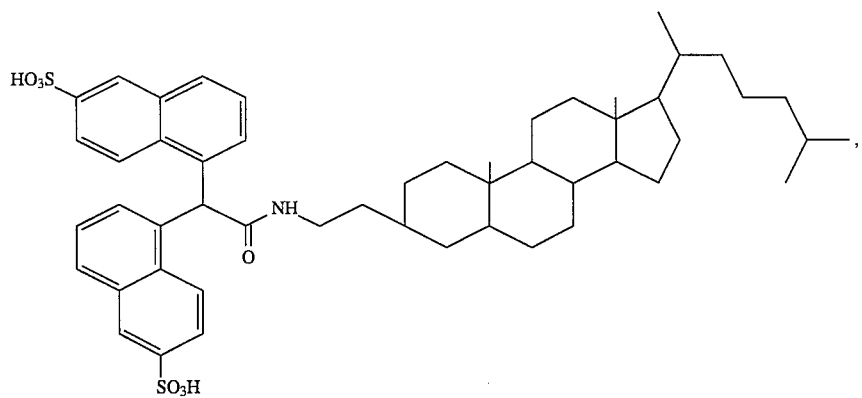

-continued

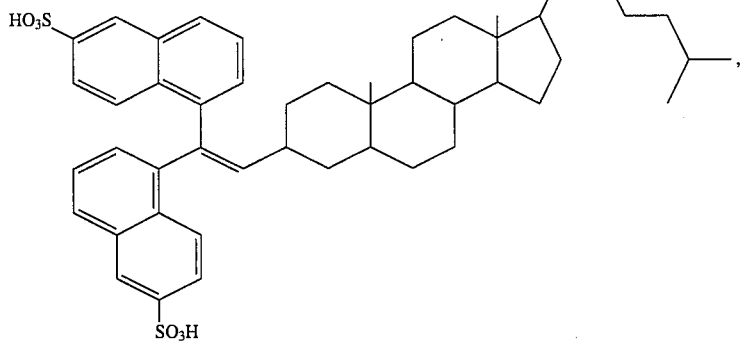

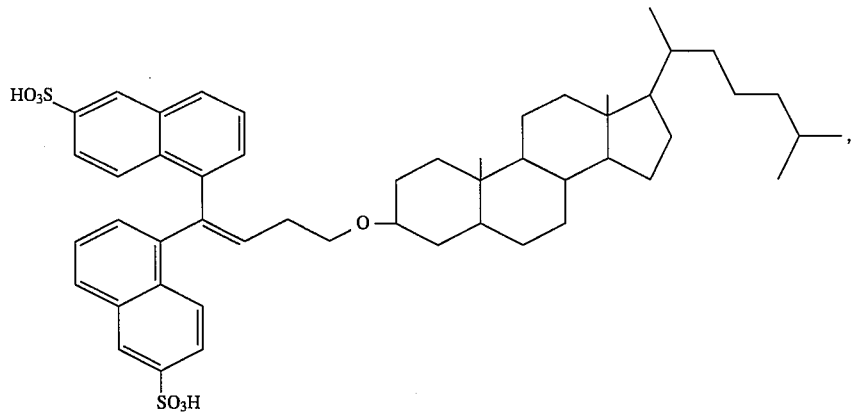

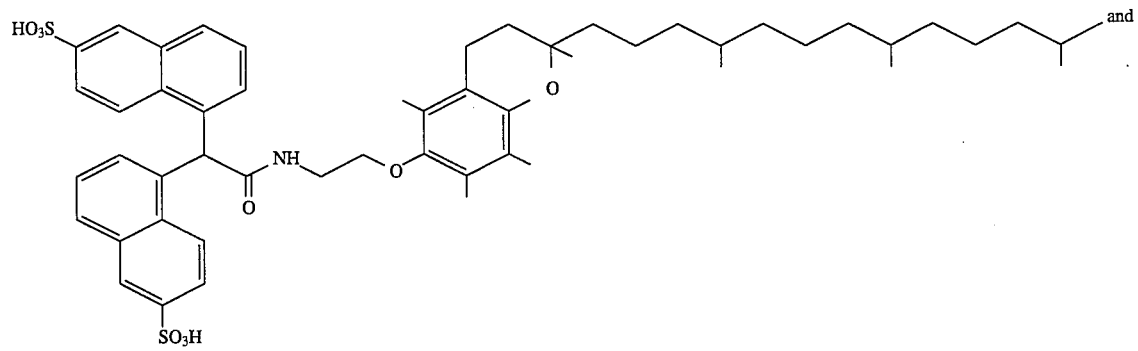

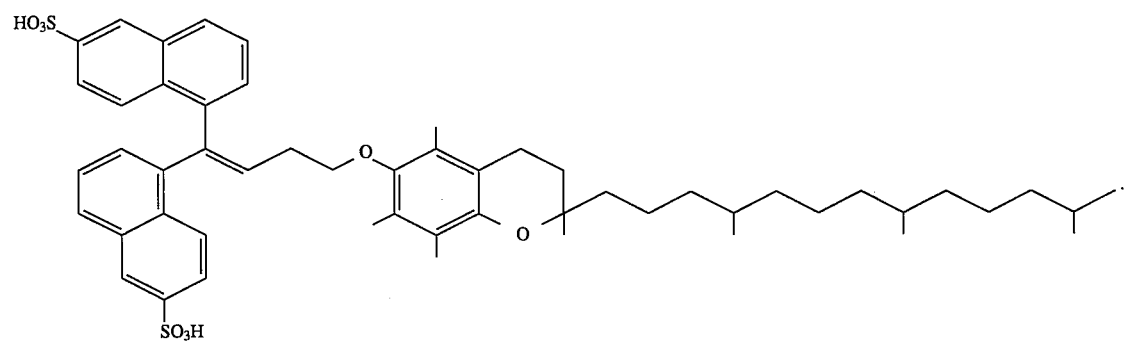

5. The method of claim 3 wherein the pro-drug is administered orally.

6. The method of claim 1 wherein the drug is selected from the group consisting of cefonicid, sulfamazone, cefpimizole, sulbenicillin, acamprosate, dipyrone, taurosteine, glutaurine, solasulfone, dibupyrone, methaniazide, dicresulene and cefsulodin.

7. A pro-drug comprising a substituted neopentyl sulfonate ester of a drug having one or more sulfonic acid functional groups;

wherein the substituent is a protected nucleophilic group that is capable of being deprotected in vivo; and wherein the nucleophilic group is suitably situated so that after being deprotected it is capable of displacing the sulfonate group by internal nucleophilic attack at the ester carbon to which the sulfonate group is bonded.

8. The pro-drug of claim 7 wherein the substituted-neopentyl sulfonate ester has the following structural formula:

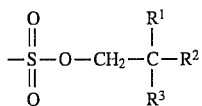

wherein $R^1$ and $R^2$ are independently selected from the group consisting of substituted or unsubstituted lower alkyl, aryl substituted alkyl, heteroaryl substituted alkyl; in the alternative, $R^1$ and $R^2$ taken together can be cycloalkyl;

wherein $R^3$ is a protected nucleophilic group capable of being deprotected in vivo or a lower alkyl group substituted by a nucleophilic group that is protected with a group capable of being removed in vivo.

9. The pro-drug of claim 8 wherein $R^1$ and $R^2$ are each methyl and $R^3$ is a lower alkyl substituted by trialkylsilyloxy, triarylsilyloxy, aryldialkylsilyloxy, alkyldiarylsilyloxy, —$SR^6$, —$SCONHR^5$, —$OCOR^5$, —$OCOOR^5$, —$OR^6$, —$NR^7CHO$, —$NR^7COR^5$, —$NR^7COOR^5$ or —$NR^7R^8$;

wherein $R^5$ is selected from the group consisting of substituted or unsubstituted aryl, heteroaryl, lower alkyl, aryl substituted alkyl and heteroaryl substituted alkyl;

wherein $R^6$ is an alcohol or thiol protecting group;

wherein $R^7$ is hydrogen or a lower alkyl group; and wherein $R^8$ is an amine protecting group.

10. The pro-drug of claim 9 wherein the drug is selected from the group of compounds having the following structural formula:

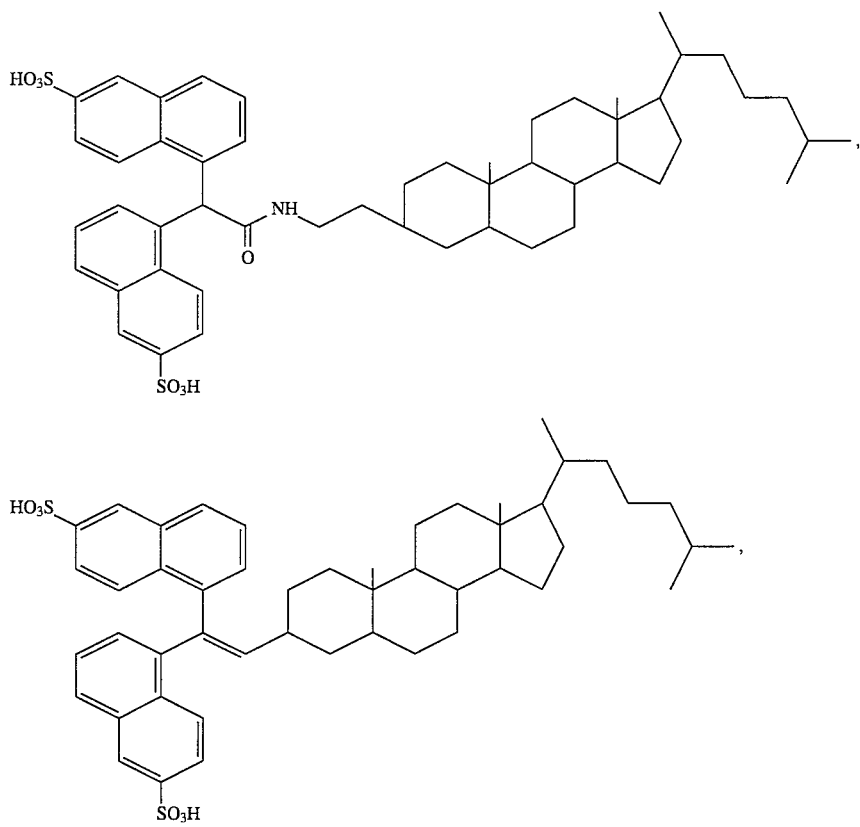

-continued
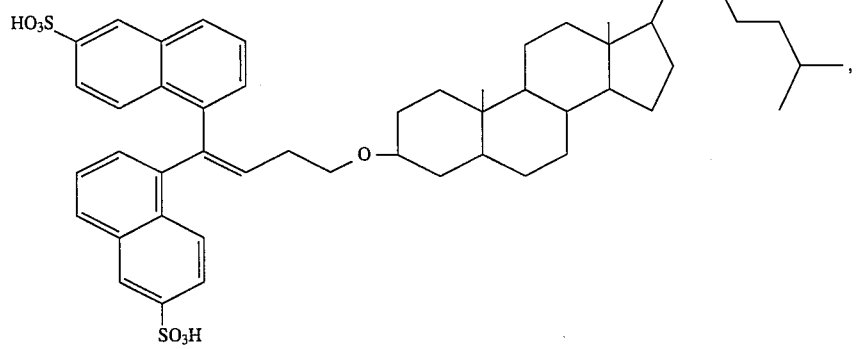
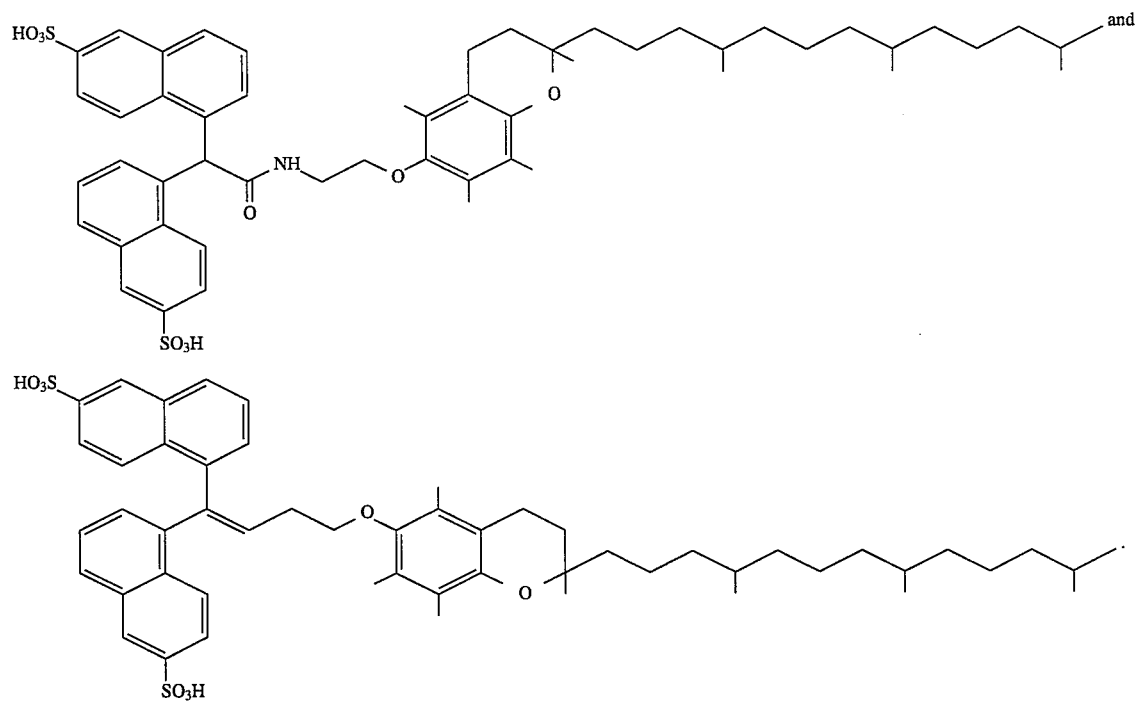
11. The pro-drug of claim 7 wherein the drug is selected from the group consisting of cefonicid, sulfamazone, cefpimizole, sulbenicillin, acamprosate, dipyrone, taurosteine, glutaurine, solasulfone, dibupyrone, methaniazide, dicresulene and cefsulodin.
* * * * *